United States Patent [19]
Ito et al.

[11] Patent Number: 5,685,823
[45] Date of Patent: Nov. 11, 1997

[54] END STRUCTURE OF ENDOSCOPE

[75] Inventors: Keiji Ito; Shinichi Matsuno, both of Tokyo, Japan

[73] Assignee: Asahi Kogaku Kogyo Kabushiki Kaisha, Tokyo, Japan

[21] Appl. No.: 408,886

[22] Filed: Mar. 24, 1995

[30] Foreign Application Priority Data

Mar. 30, 1994 [JP] Japan ................................ 6-059641

[51] Int. Cl.⁶ .................................................... A61B 1/04
[52] U.S. Cl. ...................... 600/127; 600/121; 600/129; 600/156; 600/157
[58] Field of Search .................... 600/121, 123, 600/125, 127, 129, 153, 156, 157, 158, 203, 187, 205, 188; 433/93, 180; 138/89.3, 89.4, 96 R, 118.1, 147; 128/912; 220/449, 669, 675, DIG. 21

[56] References Cited

U.S. PATENT DOCUMENTS

| | | | |
|---|---|---|---|
| D. 264,494 | 5/1982 | Chapa | 138/96 R |
| 3,980,078 | 9/1976 | Tominaga | 600/157 |
| 4,794,911 | 1/1989 | Okada | 600/127 |
| 4,881,810 | 11/1989 | Hasegawa | 600/127 X |
| 4,991,565 | 2/1991 | Takahashi et al. | |
| 5,154,164 | 10/1992 | Chikama | 600/125 X |
| 5,193,525 | 3/1993 | Silverstein et al. | 600/123 X |
| 5,305,736 | 4/1994 | Ito | |
| 5,325,847 | 7/1994 | Matsuno | |
| 5,329,935 | 7/1994 | Takahashi | 600/121 |
| 5,419,311 | 5/1995 | Yabe et al. | 600/124 |

FOREIGN PATENT DOCUMENTS

| | | | |
|---|---|---|---|
| 60-15529 | 5/1985 | Japan | |
| 0646804 | 2/1989 | Japan | |
| 5-38321 | 2/1993 | Japan | 600/121 |
| 0543375 | 7/1993 | Japan | |
| 6-14865 | 1/1994 | Japan | 600/127 |
| 7171091 | 7/1995 | Japan | |

*Primary Examiner*—Beverly M. Flanagan
*Attorney, Agent, or Firm*—Greenblum & Bernstein P.L.C.

[57] ABSTRACT

An end structure of an endoscope includes a front end body of a cylindrical insertion portion to be inserted in a human body, a fluid discharge opening which opens into the front end body, a front end cap detachably attached to the front end body and having a fluid injection nozzle connected to the fluid discharge opening. A projection is provided on the end cap, is fitted in the fluid discharge port, and constitutes at least a part of the fluid injection nozzle.

15 Claims, 8 Drawing Sheets

END STRUCTURE OF ENDOSCOPE

BACKGROUND OF THE INVENTION

1. Field of the Invention

The present invention relates to an end structure of an endoscope to be inserted in a human body, and more precisely, it relates to a structure of a fluid injection nozzle thereof or its surrounding area.

2. Description of Related Art

In general, a conventional endoscope is provided with a relatively soft front end cap which is detachably attached to a front end of a rigid insertion portion of the endoscope to be inserted in a human body. The front end of the rigid insertion portion is provided with an air/water outlet opening (fluid discharge opening) from which air and water are discharged, or a water outlet opening (fluid discharge opening) from which water is discharged. The front end cap is provided with a fluid injection nozzle which is connected to the fluid discharge opening when the front end cap is attached to the front end of the insertion portion. It is necessary to provide a positioning mechanism between the front end cap and the front end of the insertion portion to determine a relative position therebetween in the circumferential direction to thereby register the nozzle of the front end cap with the fluid discharge opening of the insertion portion. However, even if the injection nozzle of the front end cap is registered with the fluid discharge opening of the insertion portion, all the fluid discharged from the fluid discharge opening is not always introduced into the injection nozzle of the front end cap. Specifically, since the front end cap is merely pressed against the front end of the insertion portion due to a resilient force, the fluid can be partially discharged through a possible gap or clearance between the front end cap and the front end of the insertion portion.

SUMMARY OF THE INVENTION

A primary object of the present invention is to provide an end structure of an endoscope in which fluid discharged from a fluid discharge opening of a front end body of an insertion portion of the endoscope can be positively introduced into a fluid injection nozzle of a front end cap.

Another object of the present invention is to provide an end structure of an endoscope in which the positioning of a front end cap and a front end body of an insertion portion of the endoscope in a circumferential direction can be reliably effected.

To this end, according to the present invention, there is provided an end structure of an endoscope which includes a front end body of a cylindrical insertion portion to be inserted in a human body, a fluid discharge opening which opens into the front end body, a front end cap detachably attached to the front end body and having a fluid injection nozzle which can be connected to the fluid discharge opening, and a projection which is provided on the end cap to be fitted in the fluid discharge port and which constitutes at least a part of the fluid injection nozzle.

Preferably, the fluid discharge opening is formed by an air/water injection nozzle or a water injection nozzle.

The fluid discharge opening and the fluid injection nozzle can be provided on the front end surface of the front end body, or on the cylindrical front end body at an eccentric position. Alternatively, the fluid discharge opening and the fluid injection nozzle can be provided on the side surface of the front end body.

Preferably, the front end cap is provided on the outer peripheral surface thereof with a recess in which a disengaging tool can be engaged to remove the front end cap from the front end body.

The front end body and the front end cap can be provided with marks that indicate a fitting position of the front end body and the front end cap in the circumferential direction.

The marks can be formed by a first recess formed on the outer surface of the front end cap, so that a disengaging tool can be engaged in the recess to remove the front end cap from the front end body, and a second recess formed on the front end body so that the first recess can be engaged by the second recess.

According to another aspect of the present invention, there is provided an end structure including a front end body of a cylindrical insertion portion to be inserted in a human body, and a front end cap detachably attached to the front end body, wherein the front end cap and the front end body are provided with marks that indicate a fitting position of the front end cap and the front end body in the circumferential direction.

In this aspect, the marks can be formed by a first recess formed on the outer surface of the front end cap, so that a disengaging tool can be engaged in the recess to remove the front end cap from the front end body, and a second recess formed on the front end body so that the first recess can be engaged by the second recess.

The present disclosure relates to subject matter contained in Japanese Patent Application No. 6-59641 (filed on Mar. 30, 1994) which is expressly incorporated herein by reference in its entirety.

BRIEF DESCRIPTION OF THE DRAWINGS

The invention will be described below in detail with reference to the accompanying drawings, in which.

DESCRIPTION OF THE PREFERRED EMBODIMENT

Figure 1:
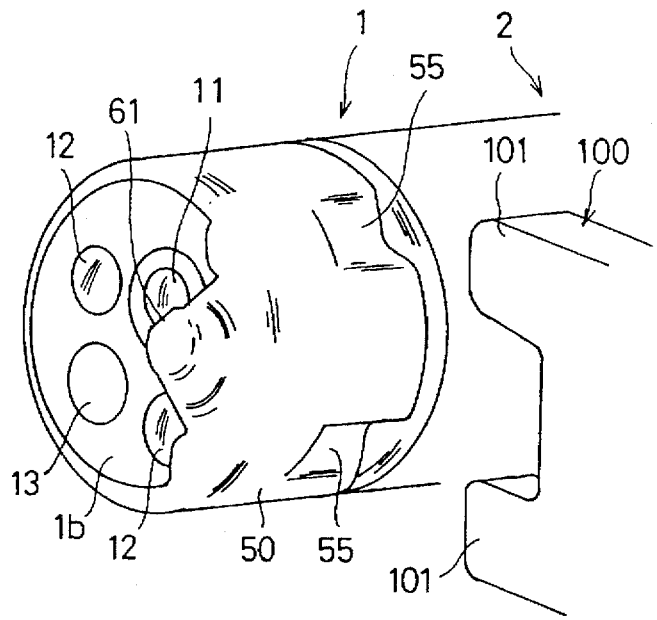
FIG. 1 is a perspective view of a first embodiment of an end structure of the present invention.
Figure 2:
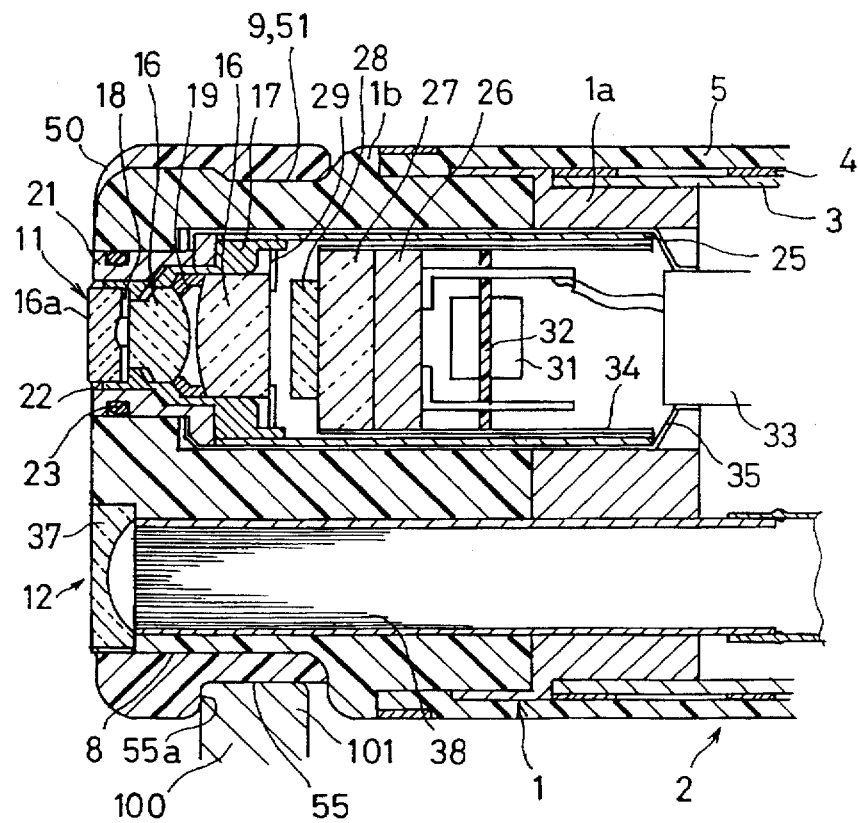
FIG. 2 is a sectional view of an end structure taken along the line A-B-C-D-E-F-G-H in FIG. 3.

FIGS. 1 through 6 show a first embodiment of the present invention. As shown in FIG. 2, a front end body 1 is connected to a front end portion of a bendable portion 2 provided at a front end of an insertion portion which is made of an elongated flexible tube. The bendable portion 2 can be optionally bent by a remote control operation.

The bendable portion 2 includes a number of articulated rings 3 which are rotatably connected to each other by rivets (not shown), a tubular net 4 which surrounds the articulated rings 3, and a rubber tube 5 which surrounds the tubular net 4. The rubber tube 5 is fastened and adhered onto the outer peripheral surface of the front end body 1.

The front end body 1 is includes a metal block portion 1a made of stainless steel which is connected to the front end of the bendable portion 2 so that the metal block portion 1a is not exposed to the outside, and a plastic block portion 1b which is secured to the front end of the metal block portion 1a so that the plastic block portion is exposed to the outside.

Figure 3:
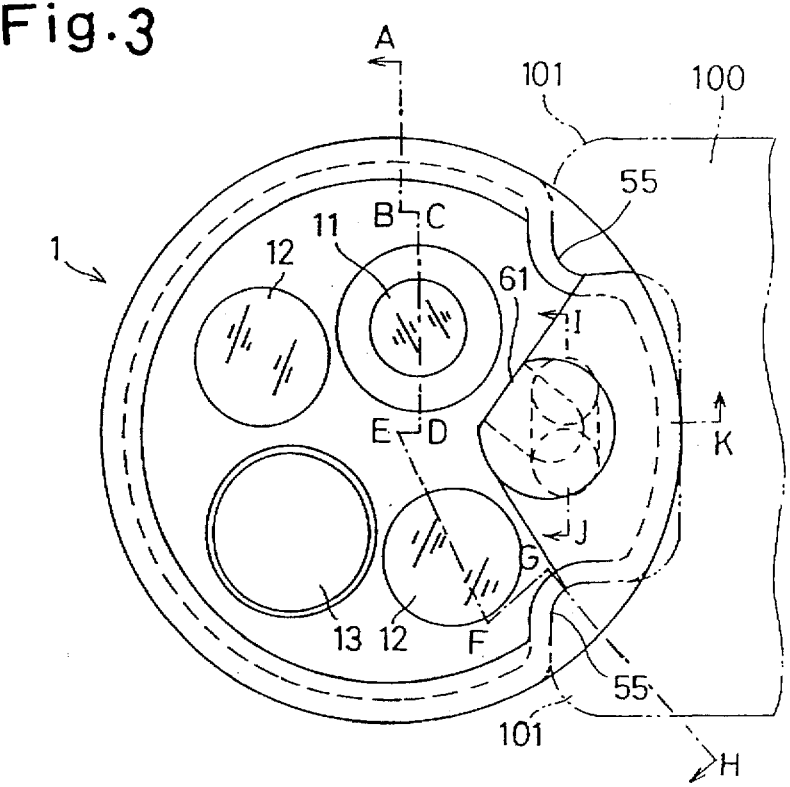
FIG. 3 is a front elevational view of the end structure shown in FIG. 1.

In the illustrated embodiment, the endoscope is a so-called front-view type endoscope in which the front portion of the tube axis is viewed. As can be seen in FIG. 3, the endoscope is provided, on the front end surface of the front end body 1, with a view window 11, illumination windows 12, and a forceps channel outlet opening 13.

As shown in FIG. 2, an objective optical system 16 is provided within the view window 11 to be secured to and in a metal lens frame 17. The first lens (frontmost lens) 16a is caulked to the lens frame 17 at an intermediate stepped portion thereof. Reference numerals 18 and 19 designate an aperture diaphragm and a spacer, respectively.

An insulation ring 21 which is made of, for example, electrically insulating plastic is secured to the front end of the outer peripheral surface of the lens frame 17. The insulation ring 21 is provided with a recess which is filled with epoxy resin adhesive 22, so that the front end of the lens frame 17 is not exposed. The outer peripheral surface of the insulation ring 21 is fitted in a hole formed in the plastic block portion 1b of the front end body 1 through a sealing O-ring 23 provided therebetween.

The lens frame 17 is provided, on the rear portion of the outer peripheral surface thereof, with a metal shield pipe 25 fitted and secured thereto, which is integrally provided therein with a solid state image pickup device 26 which is made of, for example, a solid state charge coupled device (CCD) with an image receiving surface being oriented forward.

In front of the CCD 26 there is provided a transparent glass cover 27 which is secured to a YAG laser cut filter 28 located in front thereof. Consequently, an image of an object to be observed is transmitted through the transparent elements 27 and 28 and is formed on the light receiving surface of the solid state image pickup device 26 by the objective optical system 16. Reference numeral 29 designates a light intercepting mask.

There is, in the shield pipe 25, an electronic element 31 mounted to a printed circuit board (PCB) 32 to process signals to be supplied to or from the solid state image pickup device 26 behind the latter. A signal cable 33 extends rearwardly from the PCB 32.

The elements within the shield pipe 25 and the shield pipe 25 are surrounded at the outer peripheral surfaces thereof by insulation tapes 34 and 35 wound thereabout to establish an electrical insulation between the inside area of the shield pipe 25 and the shield pipe elements, and between the outside area of the shield pipe and the shield pipe 25. The rear end of the insulation tape 35 outside the shield pipe 25 extends to the front end portion of the outer peripheral surface of the signal cable 33 to cover the same.

The present invention can be applied to an endoscope having an optical image transmitting mechanism using a bundle of image guide optical fibers in place of the solid state image pickup device 26 as mentioned above, or also can be applied to a sclerotic endoscope.

To increase the orientation angle of the illuminating light, the emission end of a bundle of illuminating light guide optical fibers inserted in the insertion portion of the endoscope is located at the inner end of a concave lens 37 mounted to and within the illumination window 12.

Figure 4:
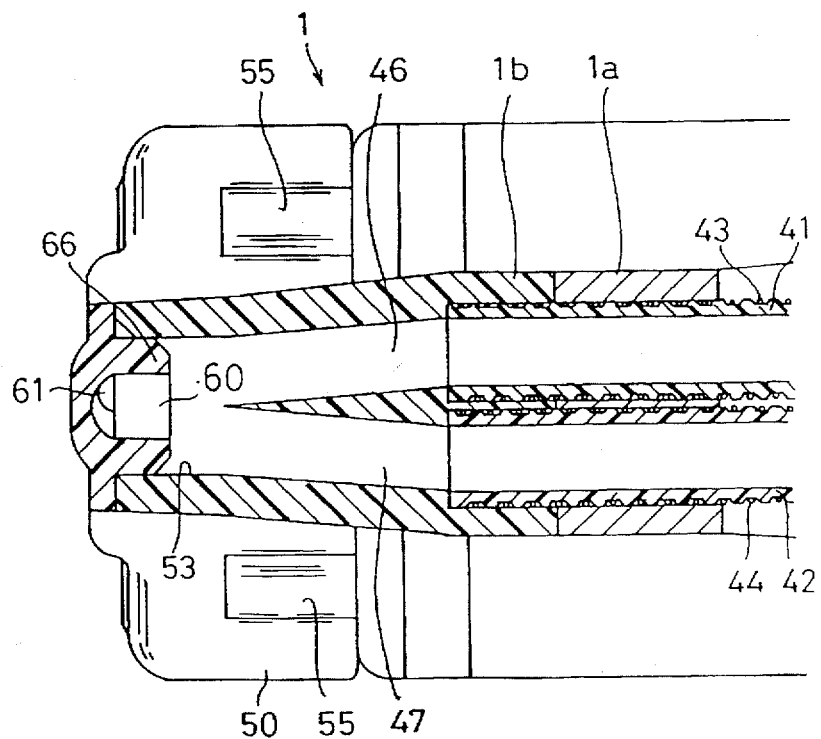
FIG. 4 is a sectional view of an end structure taken along the line I-J in FIG. 3.
Figure 5:
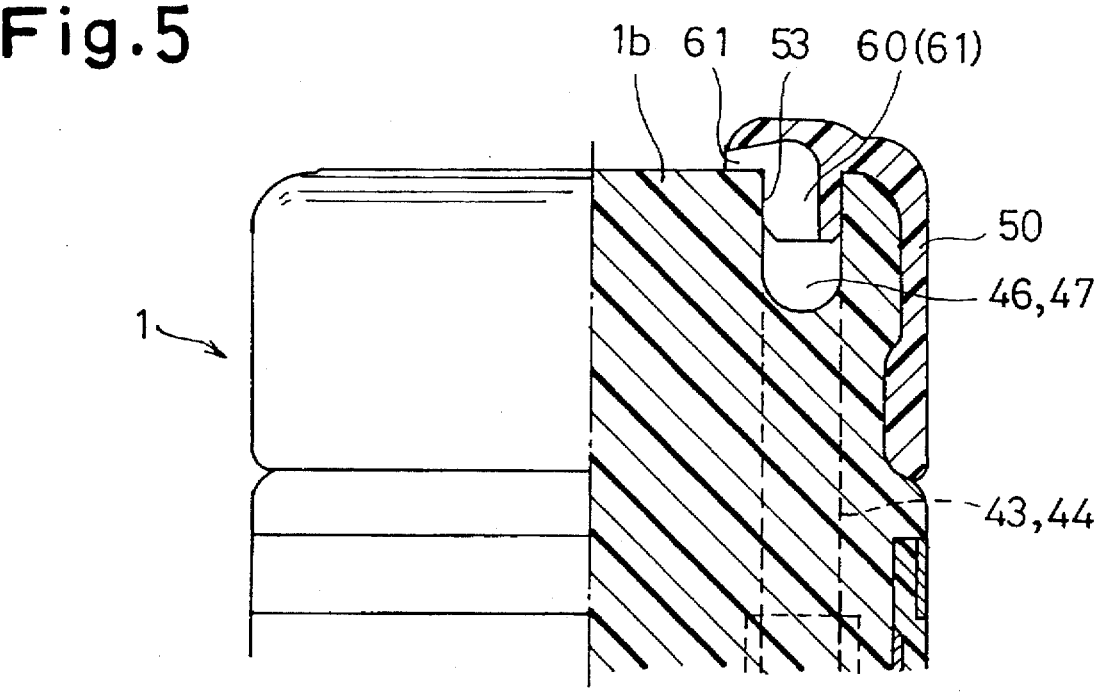
FIG. 5 is a sectional view of an end structure taken along the line E-K in FIG. 3.

An air supply tube 41 and a water supply tube 42 are provided in the bendable portion 2 (FIG. 4). An air discharge opening (passage) 46 and a water discharge opening (passage) 47 are formed in the front end body 1, so that the air supply tube 41 and the water supply tube 42 are connected to the air discharge passage 46 and the water discharge passage 47, respectively. The air supply tube 41 and the water supply tube 42 terminate at a common fluid discharge opening or port 53 which opens into the front end surface of the front end body 1. The air supply tube 41 and the water supply tube 42 are made of ethylene tetrafluoride and are provided with outer peripheral helical grooves within the bendable portion 2, so that spring wires 43 and 44 are wound along the helical grooves to prevent the air supply tube 41 and the water supply tube 42 from bending.

A front end cap 50 made of a non-conducting and resilient material, such as polyurethane rubber, is attached to the outer peripheral surface of the plastic block portion 1b of the front end body 1 from the front side.

The front end cap 50 is in the form of a cylinder whose outer diameter is substantially identical to the outer diameter of the front end body 1 and has at the rear end a circular opening.

The front end cap 50 is provided with a projection 60 which can be fitted in the common fluid discharge opening 53 of the front end body 1 and a fluid injection nozzle 61. The fluid injection nozzle 61 is provided with an inner end formed within the projection 60 and a generally L-shaped (in section, see FIG. 8) outer end extending into the view window 11.

As may be seen from the foregoing, since the front end cap 50 is provided with the projection 60 which is fitted in the fluid discharge opening 53 and which constitutes at least a part of the fluid injection nozzle 61, air and water to be supplied through the air supply tube 41 and the air discharge passage 46 and the water supply tube 42 and the water discharge passage 47, respectively, are positively introduced into the fluid injection nozzle 61 to supply the same to the view window 11. Hence, there is no leakage of air or water through the gap between the front end body 1 and the front end cap 50, etc. Moreover, since the fluid discharge opening 53 is located eccentric with respect to the axis of the front end body 1 which is usually cylindrical, the positioning of the front end cap 50 relative to the front end body 1 in the circumferential direction can be reliably effected by fitting the projection 60 in the discharge opening 53.

Note that all the edge lines of the front end cap 50 are smoothly rounded or chamfered so as not to cause injury to the mucous membrane within the body cavities of a patient.

The endoscope illustrated in the drawings is provided with a structure or mechanism to facilitate the attachment or detachment of the front end cap 50 to or from the front end body 1 and thereby ensure an easy verification of the fitting position of the front end cap 50 and the front end body 1 in the circumferential direction.

To this end, the front end cap 50 is provided, on the rear portion of the inner peripheral surface thereof, with an inwardly projecting projection 51 which is tightly fitted in a circumferential recessed groove 9 formed on the outer peripheral surface of the plastic block portion 1b of the front end body 1 (FIG. 2).

Consequently, upon attaching the front end cap 50 to the front end body 1, the inner projection 51 of the front end cap 50 is moved along and onto the front end body 1 from the front side, while elastically deforming (expanding) the front end cap 50.

As a result, the front end body 1 is forced into the end cap 50. As soon as the inner projection 51 of the front end cap 50 is fitted in the recessed groove 9 of the front end body 1, the front end cap 50 is returned to its original shape due to the elastic restoring force, as shown in FIG. 2, so that the end cap 50 is prevented from being accidentally disengaged or detached from the front end body 1. In this state, there is little or no space between the outer peripheral surface of the front end cap 50 and the outer peripheral surface of the front end body 1. Namely, the outer peripheral surface of the front end cap 50 is substantially flush with the outer peripheral surface of the front end body 1.

As can be seen in FIGS. 2 and 3, the front end cap 50 is provided, on the rear portion of the outer peripheral surface thereof, with a pair of circumferentially spaced recesses 55, 55, each having a general L-shape with round corners in a front elevation as shown in FIG. 3. In the side elevation shown in FIG. 2, each of the recesses 55 is provided on the front end thereof with a front wall 55a which is substantially vertical with respect to the outer peripheral surface of the front end cap 50. The rear end of each recess 55 terminates at the rear end of the front end cap 50 without a space.

Figure 6:
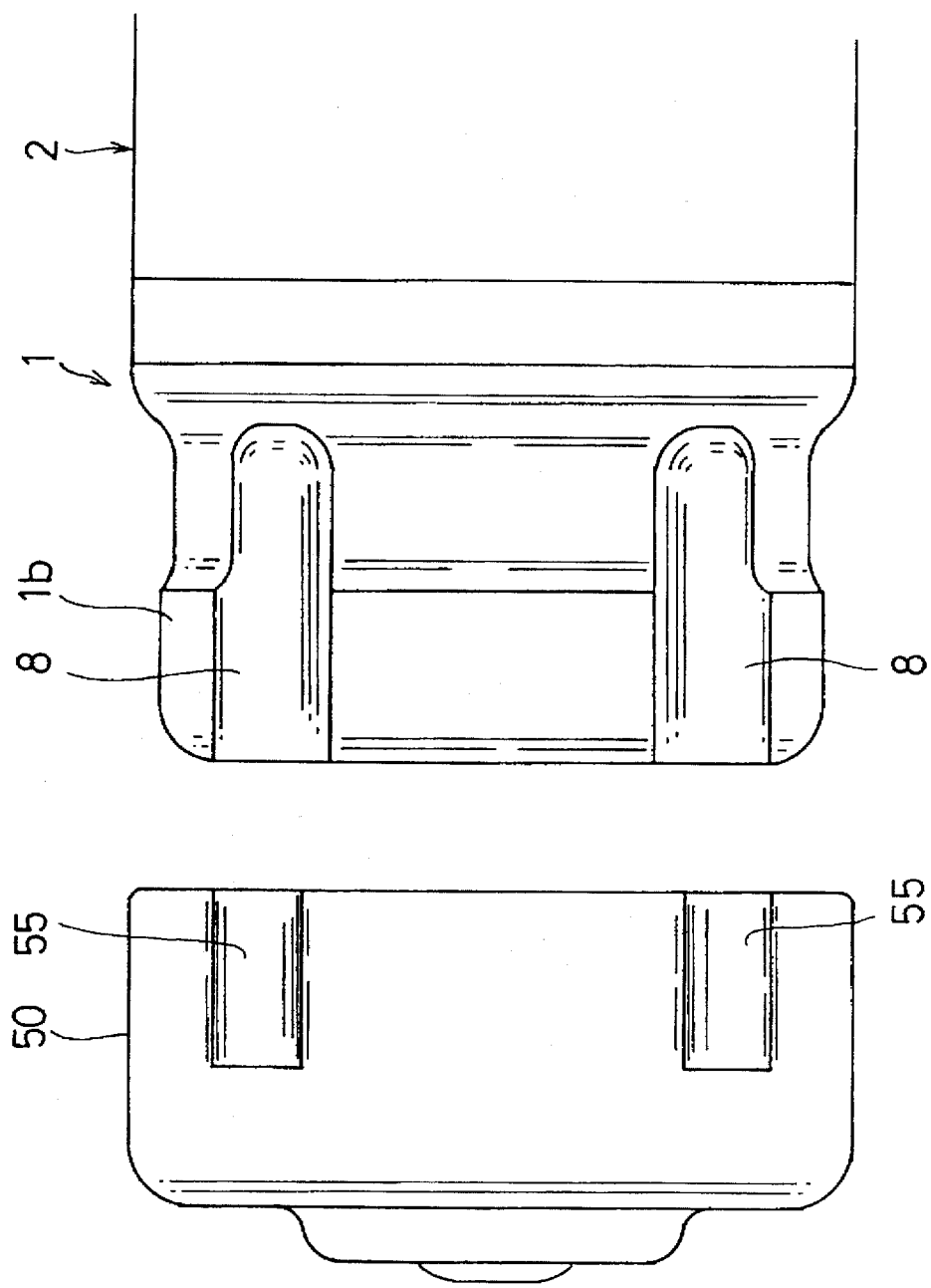
FIG. 6 is a side elevational view of the end structure shown in FIG. 1, with a removed end cap.

To prevent the recesses 55 from interfering with the front end body 1 upon attachment or detachment of the front end cap 50 to or from the front end body 1, the front end body 1 is provided with recesses 8, 8 whose sectional shape is identical to the corresponding recesses 55, 55 as shown in FIGS 2 and 6. The recesses 8 linearly extend rearwardly from the front end of the front end body 1.

There are no recesses 55 on the front end portion of the outer peripheral surface of the front end cap 50, but there are projections corresponding to the recesses 55 on the inner peripheral surface of the end cap 50, so that the projections can be fitted in the recesses 8 of the front end body 1.

Consequently, upon attachment of the front end cap 50 to the front end body 1, when the recesses 55 are registered with the corresponding recesses 8, the relative position therebetween in the circumferential direction is automatically determined. Once the front end cap 50 is attached to the front end body 1, the engagement of the recesses 8 and 55 prevents the front end cap 50 from rotating with respect to the front end body 1 about the axis thereof. Namely, the recesses 8 of the front end body 1 and the recesses 55 of the front end cap 50 function as indication marks that determine the relative position therebetween in the circumferential direction.

Bifurcated arms 101, 101 of a disengaging or detaching tool 100 can be engaged in the recesses 55 of the front end cap 50 to remove the front end cap 50 from the front end body 1, as shown in FIG. 1 or 3. The tool 100 is made of metal or hard plastic. The bifurcated arms 101 are spaced such that they can be fitted in the spaced recesses 55, as shown in FIGS. 2 and 3.

When the front end cap 50 is detached from the front end body 1, the rear portion of the front end body 1 is held and pulled rearwardly by an operator's fingers, while the bifurcated arms 101 of the detaching tool 100 are engaged in the corresponding recesses 55 of the front end cap 50.

As a result, the rearward movement of the front end body 1 occurs without causing the front end cap 50, whose axial movement is restricted by the tool 100, to move. Thus, the front end cap 50 is detached from the front end body 1.

When the front end cap 50 is detached from the front end body 1, the inner projection 51 of the front end cap 50 travels over the outer peripheral surface of the front end body 1, while causing an elastic deformation of the front end cap 50.

Preferably, at least one of the front end cap 50 and the front end body 1 has a color identical to the detaching tool 100. In this connection, if detaching tools 100 having different colors are prepared depending on the kind of front end caps, a correct detaching tool 100 to be used with the associated front end cap 50 can be easily selected without fail. Alternatively, it is possible to provide marks of the same color on the detaching tool 100 and at least one of the front end body 1 and the front end cap 50.

The detached front end cap 50 can be reused after washing and disinfecting the same. Alternatively, the front end cap 50 may be of a disposable type for single use.

Figure 8:
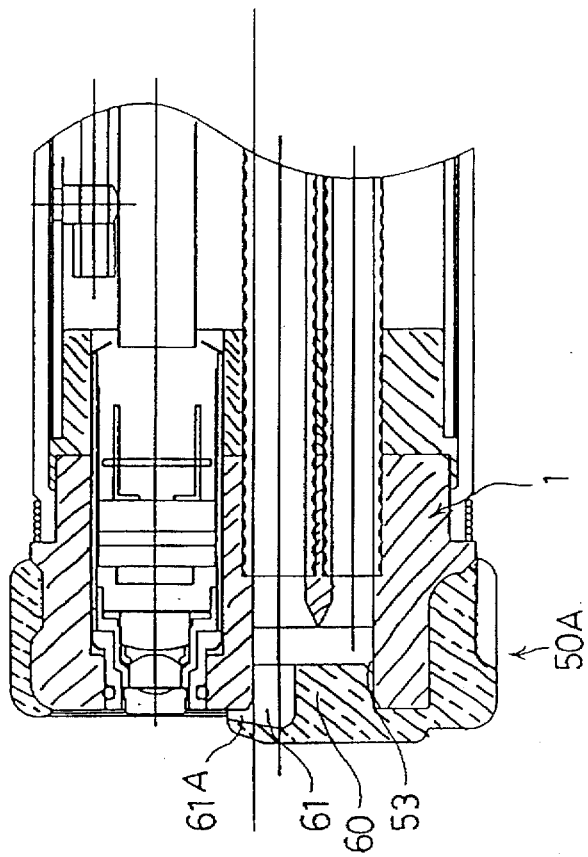
FIG. 8 is a sectional view taken along the line M-N O-P in FIG. 7.
Figure 9:
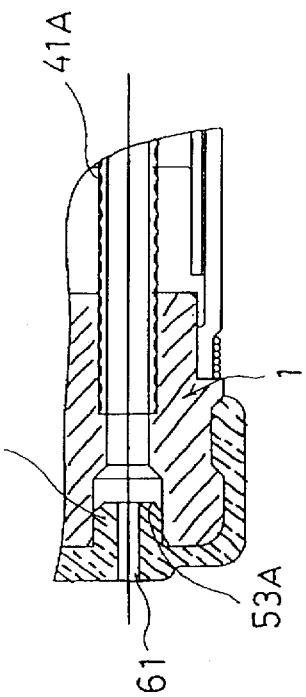
FIG. 9 is a sectional view taken along the line Q-R in FIG. 7.
Figure 7:
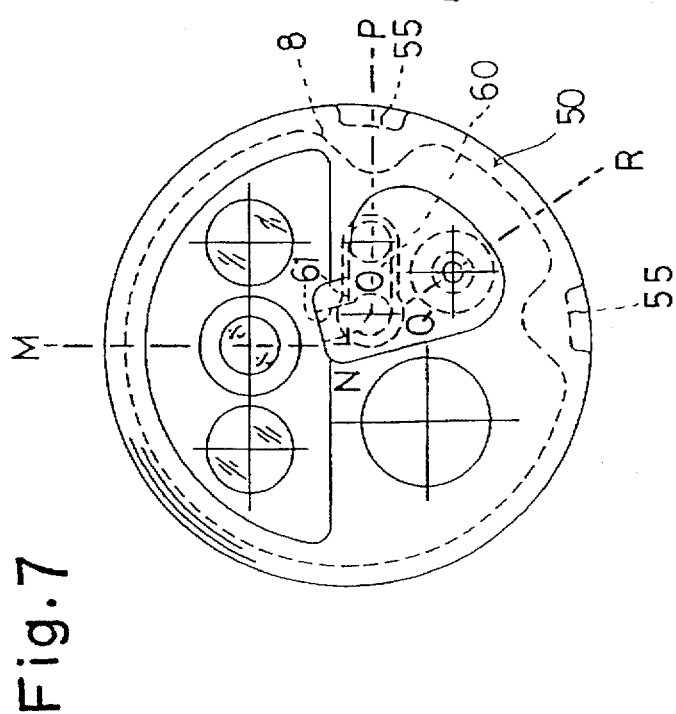
FIG. 7 is a front elevational view of a front end of an endoscope according to a second embodiment of the present invention, corresponding to FIG. 3.

FIGS. 7 through 9 show a second embodiment of the present invention. In the second embodiment, there is provided a jet nozzle for injecting water toward the front of the endoscope on the front end of the latter, in addition to the components of the first embodiment mentioned above. Specifically, the bendable portion 2 is provided with a second water supply tube 41A separate from the first water tube 41. The front end body 1 is provided with a water discharge opening (passage) 53A which is connected to the water supply tube 41A and which opens into the front end surface of the front end body 1.

The front end cap 50 is provided with a projection 60A which can be fitted in the water discharge passage 53A and which is in turn provided with the injection nozzle (water jet nozzle) 61A. The injection nozzle 61A is connected at its inner end to the water discharge passage 53A and linearly extends to open into the front end of the front end cap 50.

The other structure of the second embodiment is basically the same as the first embodiment except for the arrangement or size of the components. In the second embodiment, the components corresponding to those in the first embodiment are designated with like reference numerals.

Figure 12:
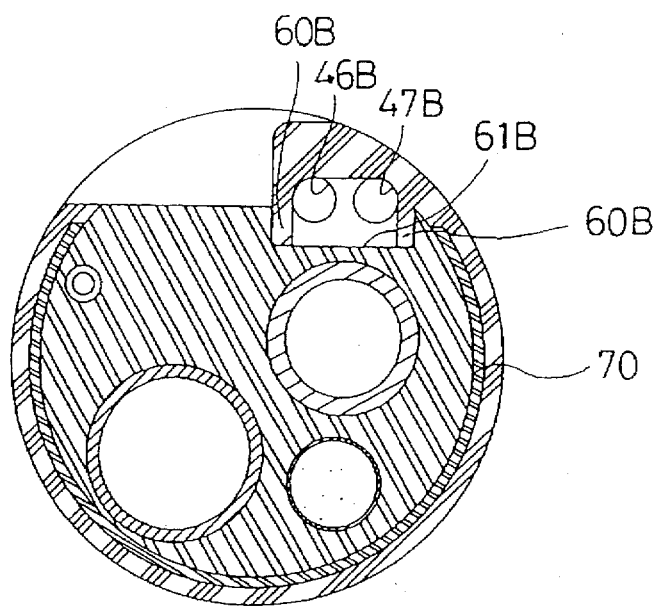
FIG. 12 is a sectional view taken along the line XII—XII in FIG. 10.
Figure 13:
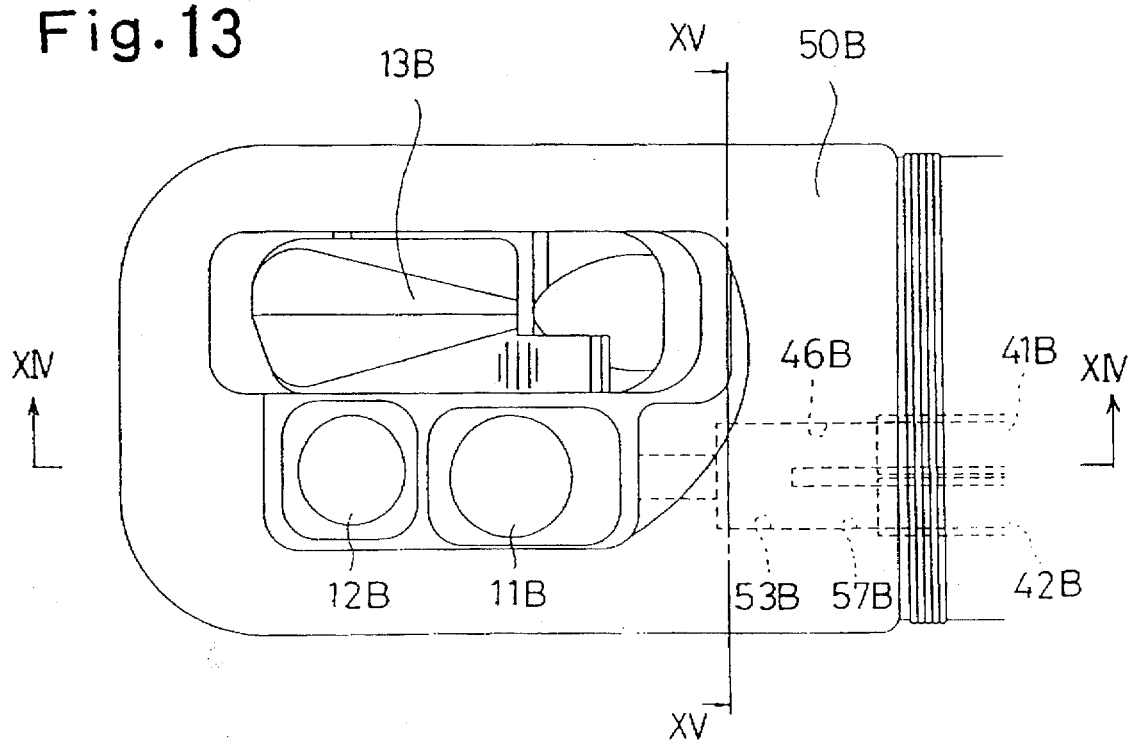
FIG. 13 is a side elevational view of a front end of an endoscope according to a fourth embodiment of the present invention.
Figure 14:
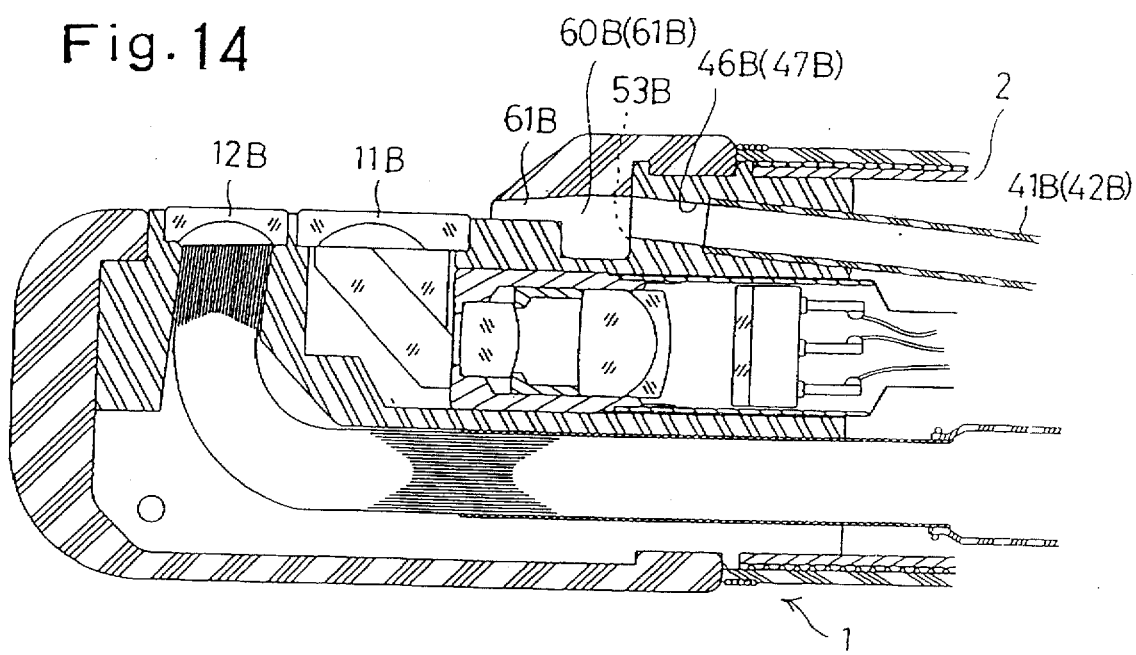
FIG. 14 is a sectional view taken along the line XIV—XIV in FIG. 13.

FIGS. 13 through 12 show a third embodiment of the present invention applied to a front end structure of a side-view type endoscope. As shown in FIGS. 13 and 14, in the side-view type endoscope, the view window 11B, the illumination window 12B and the forceps channel outlet opening 13B, etc., are provided on the side surface of the cylindrical front end body 1. The air supply tube 41B and the water supply tube 42B are provided in the bendable portion 2. The air discharge passage 46B and the water discharge passage 47B are formed in the front end body 1 to be connected to the air supply tube 41B and the water supply tube 42B, respectively. The air discharge passage 46B and the water discharge passage 47B are connected to the common fluid discharge opening 53B which opens into the side surface of the front end body 1.

The front end cap 50B which is attached to the front end body 1 is provided with a projection 60B which can be fitted in the common fluid discharge opening 53B, and a fluid injection nozzle 61B whose inner end is formed in the projection 60B. The outer end of the injection nozzle 61B opens into the view window 11B.

Figure 15:
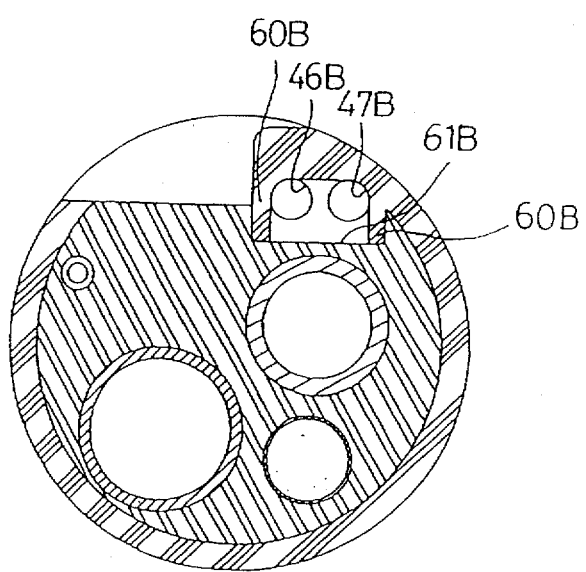
FIG. 15 is a sectional view taken along the line XV—XV in FIG. 13.

FIGS. 13 through 15 show a fourth embodiment of the present invention.

Figure 10:
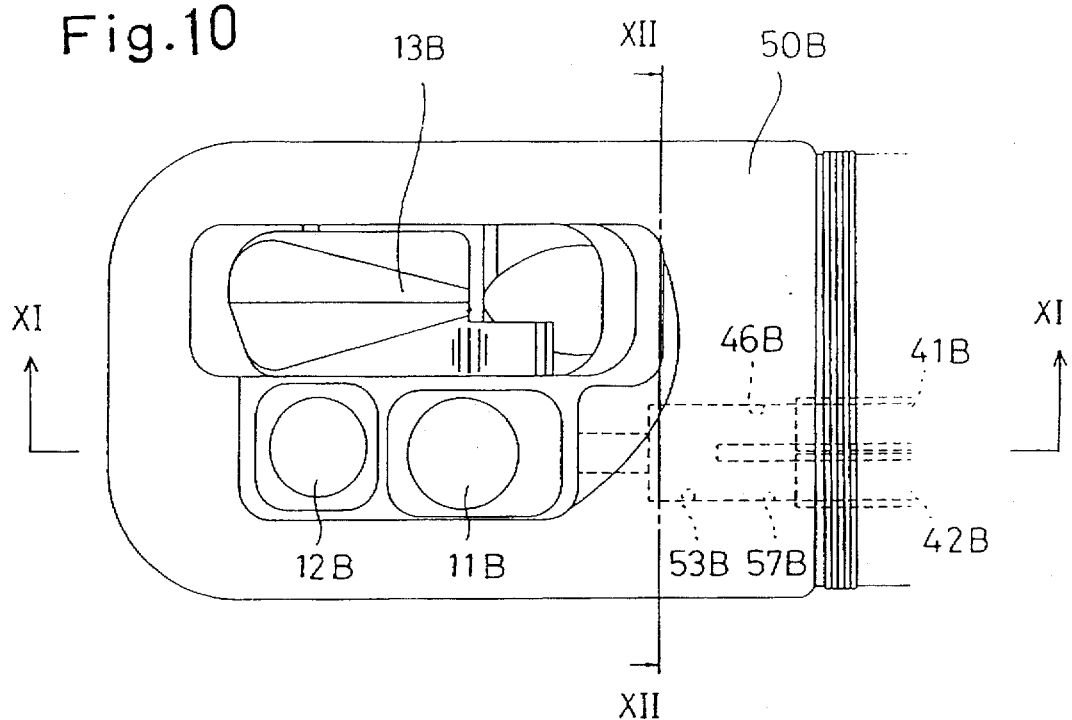
FIG. 10 is a side elevational view of a front end of an endoscope according to a third embodiment of the present invention.
Figure 11:
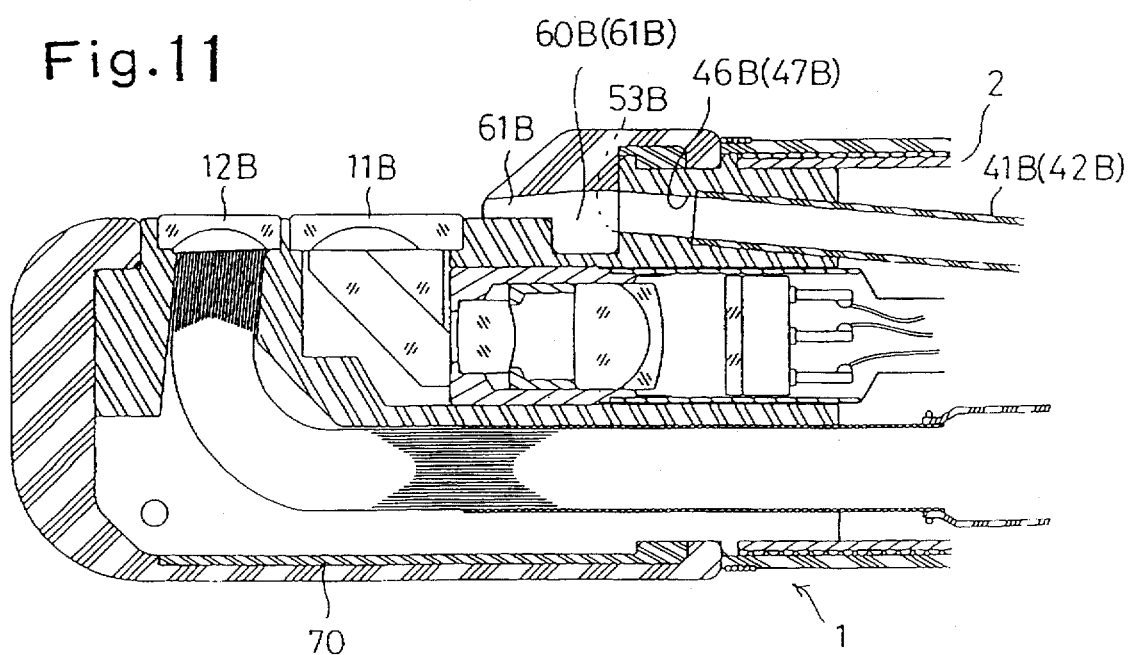
FIG. 11 is a sectional view taken along the line XI—XI in FIG. 10.

The difference between the third embodiment illustrated in FIGS. 13 through 15 and the fourth embodiment illustrated in FIGS. 10 through 12 resides only in the presence of a deformation restricting member 70 provided between the front end body 1 and the front end cap 50B in the fourth embodiment. The remainder of the structure of the fourth embodiment is substantially identical to the embodiment, provided that the endoscope in the fourth embodiment is a side-view type endoscope, as mentioned above. In the fourth embodiment, the elements corresponding to those in the first embodiment are designated with the like reference numerals.

In the second through fourth embodiments, since the projection of the front end cap is fitted in the fluid discharge opening (passage) of the front end body, and a part of the fluid injection nozzle is formed in the projection, the fluid discharged from the fluid discharge opening can be effectively introduced into the fluid injection nozzle of the front end cap. Moreover, the engagement of the projection in the fluid discharge opening ensures that the relative position between the front end body and the front end cap in the circumferential direction can be easily determined.

We claim:

1. An end structure of an endoscope comprising:

a front end body of a cylindrical insertion portion to be inserted in a human body;

a fluid discharge opening provided on a front surface of said front end body;

a front end cap detachably attached to said front end body, said front end cap including a projection, spaced from said front surface of said front end body and partially covering said front surface of said front end body; and a fluid injection nozzle, said projection and said front end body forming said fluid injection nozzle therebetween.

2. An end structure according to claim 1, wherein said fluid discharge opening comprises an air/water discharging opening.

3. An end structure according to claim 1, wherein said fluid discharge opening comprises a water discharge opening.

4. An end structure according to claim 1, wherein said fluid discharge opening and said fluid injection nozzle are provided on a front end surface of said front end body.

5. An end structure according to claim 1, wherein said fluid discharge opening and said fluid injection nozzle are provided on said front end body at a position eccentric of a center of said front end body.

6. An end structure according to claim 1, wherein said fluid discharge opening and said fluid injection nozzle are provided on a side surface of said front end body.

7. An end structure according to claim 1, wherein said front end cap is provided on an outer peripheral surface thereof with a recess in which a disengaging tool can be engaged to remove said front end cap from said front end body.

8. An end structure according to claim 1, wherein said front end body and said front end cap are provided with marks which indicate a fitting position of said front end body and said front end cap, in a circumferential direction.

9. An end structure according to claim 8, wherein said marks are formed by a first recess formed on an outer surface of said front end cap and a second recess formed on said front end body so that said first recess can be engaged by said second recess; and wherein a disengaging tool can be engaged in said first recess to remove said front end cap from said front end body.

10. An end structure according to claim 9, wherein said front end cap comprises an elastically deformable material.

11. An end structure according to claim 9, wherein at least one of said front end cap and said front end body is provided with an outer color for matching a color of the disengaging tool to be engaged therewith.

12. An end structure according to claim 9, wherein at least one of said front end cap and said front end body is provided with a mark having a color for matching a color of the disengaging tool to be engaged therewith.

13. An end structure of an endoscope comprising:

a front end body of a cylindrical insertion portion to be inserted in a human body;

a front end cap detachably attached to said front end body; and marks provided on said front end cap and said front end body, said marks indicating a fitting position of said front end cap and said front end body in a circumferential direction;

wherein said marks are formed by a first recess formed on an outer surface of said front end cap and a second recess formed on said front end body so that said first recess can be engaged by said second recess; and wherein a disengaging tool can be engaged in said first recess to remove said front end cap from said front end body.

14. An end structure of an endoscope comprising:

a front end body of a cylindrical insertion portion to be inserted in a human body;

an opening in a front surface of said front end body;

a front end cap detachably attached to said front end body, said front end cap including a portion, wherein said portion is insertable into said opening; and a fluid passage having a fluid emission aperture opening to said front surface of said front end body, a periphery of said fluid emission aperture formed by said portion and said opening.

15. An end structure according to claim 14, further comprising:

a fluid injection nozzle formed between said portion and said front end body.

* * * * *